United States Patent
Cohen

(10) Patent No.: US 10,279,062 B2
(45) Date of Patent: May 7, 2019

(54) SEAL FOR FILTERED VENT IN A STERILIZATION CONTAINER

(71) Applicant: INNOVATIVE STERILIZATION TECHNOLOGIES, LLC, Dayton, OH (US)

(72) Inventor: Scott Cohen, Sarasota, FL (US)

(73) Assignee: INNOVATIVE STERILIZATION TECHNOLOGIES, LLC, Dayton, OH (US)

(*) Notice: Subject to any disclaimer, the term of this patent is extended or adjusted under 35 U.S.C. 154(b) by 150 days.

(21) Appl. No.: 15/505,962

(22) PCT Filed: Aug. 20, 2015

(86) PCT No.: PCT/US2015/046115
§ 371 (c)(1),
(2) Date: Feb. 23, 2017

(87) PCT Pub. No.: WO2016/032853
PCT Pub. Date: Mar. 3, 2016

(65) Prior Publication Data
US 2017/0239381 A1 Aug. 24, 2017

Related U.S. Application Data

(60) Provisional application No. 62/041,928, filed on Aug. 26, 2014.

(51) Int. Cl.
*A61L 2/07* (2006.01)
*A61L 2/26* (2006.01)

(52) U.S. Cl.
CPC .... *A61L 2/26* (2013.01); *A61L 2/07* (2013.01); *A61L 2202/182* (2013.01)

(58) Field of Classification Search
CPC .......................................................... A61L 2/07
See application file for complete search history.

(56) References Cited

U.S. PATENT DOCUMENTS

| 4,661,326 A | 4/1987 | Schainholz |
| 4,915,913 A | 4/1990 | Williams et al. |

(Continued)

*Primary Examiner* — Donald R Spamer
(74) *Attorney, Agent, or Firm* — Standley Law Group LLP; Stephen Grant; Beverly Marsh

(57) ABSTRACT

A container (10) used for sterilizing medical instruments and the like has a sealed filtered vent. A wall or a lid of the container has a vent area formed by a plurality of holes (12) that pass therethrough. The vent area is surrounded by a convex ridge (16) on an outside surface of the container, with a corresponding concave recess (26) on an opposing inside surface. A web of filter material (36) is sized and adapted to cover the vent area and overlie the concave recess. A cover plate (37) is generally planar, with a vent area formed by a plurality of holes (38) that pass through the cover plate. This vent area is surrounded by a convex ridge (43) that is sized and adapted to correspond to the concave recess of the sterilization container. An elastomeric gasket (127) with outwardly-projecting ridges is secured to at least the convex ridge of the cover plate. A means for mounting the cover plate over the vent area of the container secures the filter material between the container vent area and the cover plate.

13 Claims, 3 Drawing Sheets

(56) References Cited

U.S. PATENT DOCUMENTS

| | | | |
|---|---|---|---|
| 5,972,196 A | * | 10/1999 | Murphy .............. B01D 53/22 |
| | | | 204/157.15 |
| 6,620,390 B1 | | 9/2003 | Wagner |
| 7,595,032 B2 | | 9/2009 | Banks |
| 2004/0011689 A1 | | 1/2004 | Bauer |
| 2004/0256268 A1 | | 12/2004 | Gleichauf et al. |
| 2005/0194387 A1 | | 9/2005 | Banks |
| 2012/0038117 A1 | | 2/2012 | Knapp |
| 2012/0039817 A1 | | 2/2012 | Vehring et al. |

\* cited by examiner

SEAL FOR FILTERED VENT IN A STERILIZATION CONTAINER

CROSS-REFERENCE TO RELATED APPLICATIONS

This application is a non-provisional patent application of U.S. 62/041,928, filed on 26 Aug. 2014, and makes a claim of priority thereto. This application incorporates the '928 provisional application by reference as if fully recited herein.

TECHNICAL FIELD

The disclosed embodiments pertain to fittings for filtered vents in containers used to sterilize surgical instruments and supplies.

BACKGROUND

Acute care facilities rely on rigid containers for the sterilization, handling and storage of surgical instrumentation and supplies. It is imperative that after sterilization, the sterile surgical instruments and supplies not be exposed to contaminates while still in the sterilization container.

Rigid sterilization containers commonly have a filtered vent (or vents) in the lid or other part of the container consisting of a patterned group of small holes. The floor of the container may also have a vent (or vents) which usually mirrors the number, size and placement of the vent or vents in the lid. One example of this is seen in U.S. Pat. No. 6,319,481, to Banks. Typically, each vent will have a sheet filter that covers the vented area and is held in place by a locking filter cover.

One commercially available sheet filter suitable for use with the present invention and with sterilization protocols is a 1.4 osy (ounces per square yard) basis weight SECURON SMS manufactured by BBA Non-Wovens. Other suitable sheet filters are also commercially available. These special filter materials are characterized by the property that they are porous at elevated temperatures to allow sterilization media to pass and non-porous at lower temperatures.

Thus, the vent, with the filter element held in place by a filter cover, allows for the entry of the sterilizing media and exit of the displaced atmosphere during the sterilization cycle. Following sterilization, the filter provides a bacterial barrier to protect the sterile integrity of the contents during storage and transport.

As the sterilizing media is introduced into the sealed container, condensation can form and collect inside the container. Retained moisture in the form of condensation may be a by-product of either steam autoclaving or alternative low temperature sterilization methods.

In addition to steam autoclaving, "flash" processing is a commonly used method of rapid steam sterilization. Since "flash" steam sterilization protocols have either a limited drying cycle or none at all, retained moisture is a persistent condition. Since bacteria have no form of self-propulsion or locomotion, they need fluid pathways or small particles as a vehicle or conduit for their movement and/or dispersal.

Whenever there is retained moisture and the floor of a container is vented, the bacterial barrier properties of the filter assembly may be immediately compromised when exposed to a non-sterile atmosphere, while still at an elevated temperature (e.g., when the sterilization container is removed from the sterilization chamber).

This situation is of special concern when retained moisture is present and the containers are handled, stored or transported while they are still hot. Containers with vented bottoms are at particular risk of contamination due to the occurrence of undetected leaking of fluid around (or through) the vents when the contents are assumed to be sterile.

Consequently, rigid sterilization containers that do not form a fluid-proof seal, as well as a particulate seal, around the filtered vents are seriously limited and may be inappropriate for the multiple sterilization methods utilized by acute care facilities.

Seals currently used for filter vents for sterilization containers are unprotected and subject to damage, which can form fluid pathways which compromise their integrity, making the containers unsafe for multiple uses. Improving the seal quality is a continuing goal in this art.

SUMMARY

This and other objectives are met by a seal as described in more detail in the following detailed description.

BRIEF DESCRIPTION OF THE DRAWINGS

A better understanding of the inventive concept and the differences from the best known prior art will be achieved by reference to the drawings filed herewith, wherein identical reference numerals are used to identify identical parts and wherein.

DETAILED DESCRIPTION

It will be understood by those skilled in the art that the present invention can and should be able to be varied in dimension, depending, in part, on the shape and size of the ventilated area to be sealed.

Further, the present invention may be applicable to a number of materials, including, but not limited to, plastic, metal or any combination thereof so long as the material is resistant to conditions imposed by sterilization methods.

In addition, while the invention is described with reference to a vent in the lid of a container, it will be recognized by those skilled in the art that the invention is equally applicable to a vent in the bottom or side of a container and that vents of different geometric patterns than that illustrated are within the scope of the invention.

Figure 1:
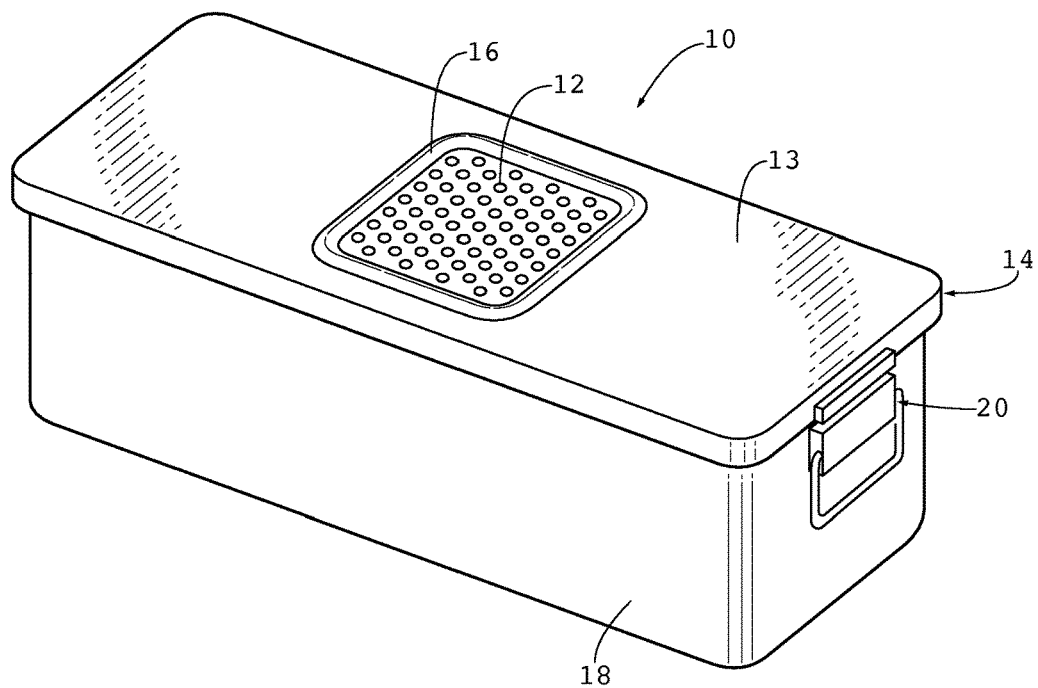
FIG. 1 is a top perspective view of a prior art rigid sterilization container having a lid with a vent formed by a pattern of small holes, as taught in U.S. Pat. No. 7,595,032 to Banks.

Referring to FIG. 1, a common design for a sterilization container 10, as taught in U.S. Pat. No. 7,595,032 to Banks ("Banks '032"), includes a vent area defined by a group of small holes 12 in the generally planar outside surface 13 of a lid 14. A convex ridge 16 in the lid 14 is provided. This convex ridge 16 can be formed by simply deforming the interior surface of the lid 14 so as to simultaneously form both a concave surface (reference number 26 in FIG. 2) below the interior surface and the convex ridge 16 above the exterior surface 13.

This bend, as will be seen in further views, provides a concave surface on the opposite side of the lid 14. On the outside surface 13 of the lid 14, the ridge 16 puts a delimiting border around the vent area and protects a filter (not seen in FIG. 1), held in place on the opposite side of the lid, by preventing objects placed on top of the lid from protruding into holes 12. It will be understood that the container body 18 and a locking means 20 for holding the container body and lid 14 together are conventional and do not require any further description. Although all structures seen in FIG. 1 are according to the prior art, none of the structures are changed in implementing the inventive concept, as will be described.

Figure 2:
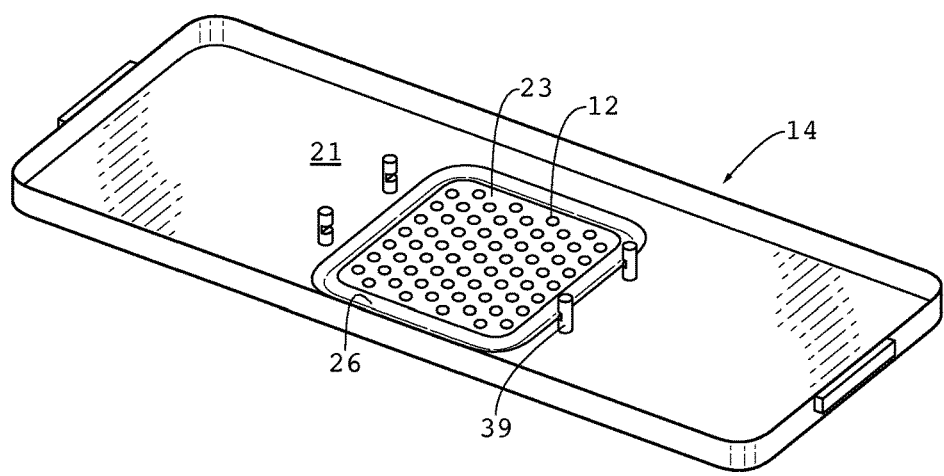
FIG. 2 is a perspective view of the underside of the removable lid of FIG. 1 rigid sterilization container, as also taught in Banks '032.

Referring to FIG. 2, which also reflects the prior art as established by Banks '032, the sterilization container lid 14 is shown removed from the container and with the container lid inverted from the position of FIG. 1. The sterilization container lid 14 has an interior surface 21, which is the "opposite" surface relative to outside surface 13 of FIG. 1. The vent area of FIG. 1 is seen in FIG. 2 as a surface 23 characterized by a plurality of holes 12 that pass entirely through the lid material. In this manner, sterilization media (such as steam) can pass into the interior of the container from the exterior. To this extent, it is notable that the vent structures being described here are not limited to being on the lid 14 of the container. The vent structures providing the inventive concept can be placed any surface of the container having sufficient area to accommodate them, especially the bottom of the container. Although vent 23 is illustrated as a pattern of holes 12 forming a generally square shape, vent 23 could just as well be a plurality of holes forming a rectangular, circular or some other shape, although a square or rectangular arrangement may have advantages. Likewise, although the holes are shown in a so-called "triangular" pitch, they could just as easily be arranged in a "square" pitch and still work with the claimed inventive concept.

Surrounding the vent 23 on the interior surface 21 is the concave surface 26 that is referred to above as being opposite to, and, indeed, the result of convex ridge 16. Also noted in FIG. 2 are posts 39, four of which are shown arranged around a perimeter defined by concave surface 26. These posts 39 function to hold a filter (not shown in FIG. 2) over the vent 23 on this interior surface 21 of the container, as will now be described.

Figure 3:
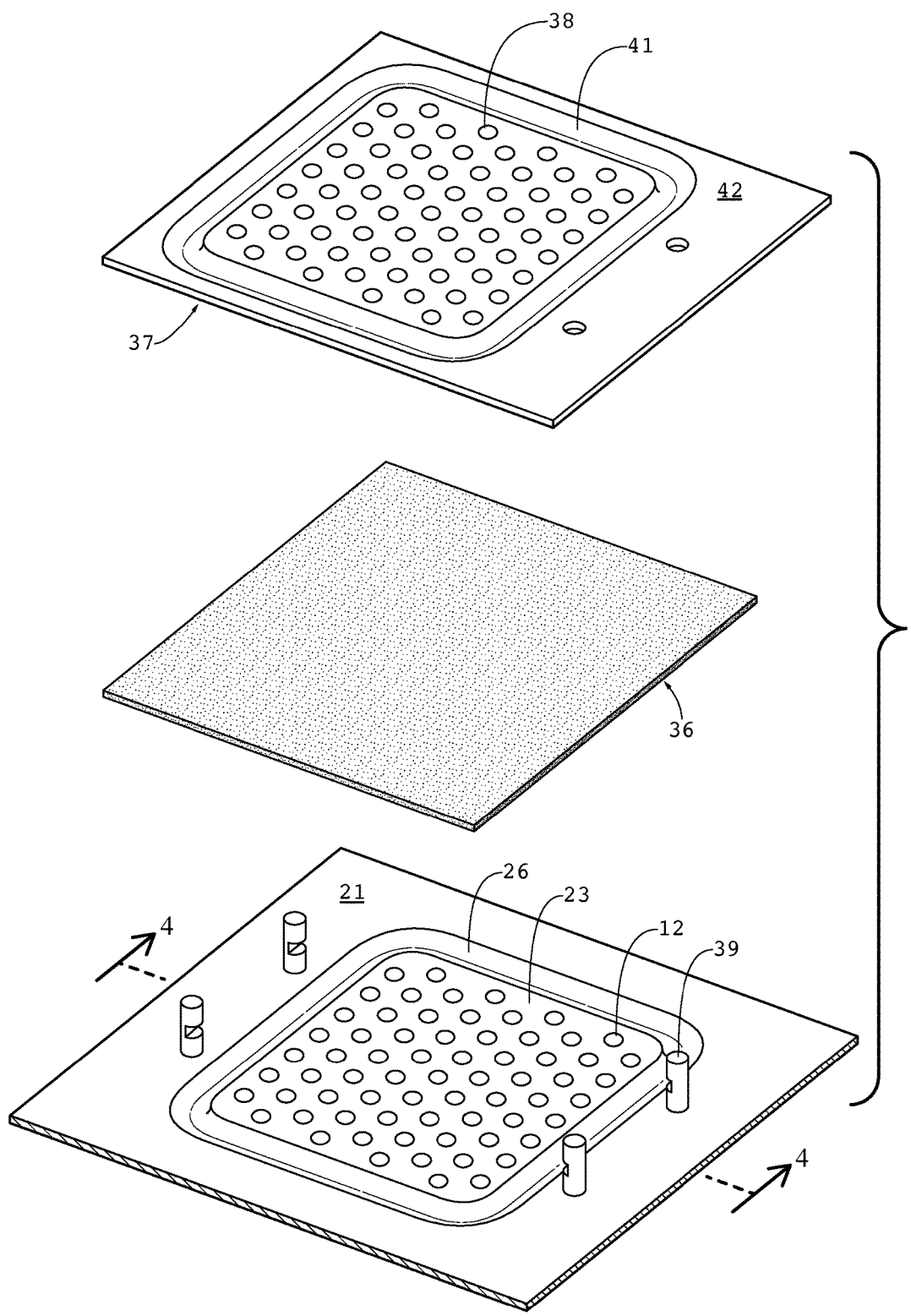
FIG. 3 is an exploded view of a vent as seen in FIG. 2 as modified by the inventive concept, with a sheet filter and a filter cover.
Figure 4:
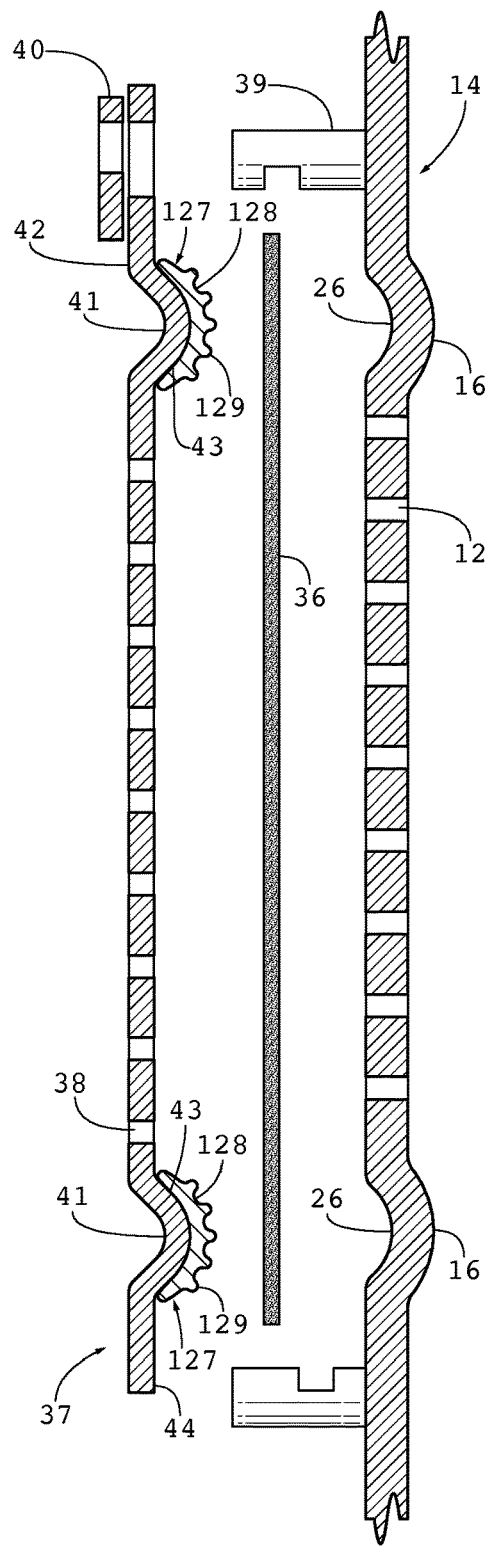
FIG. 4 is a side sectional view as would be seen along line 4-4 of FIG. 3 with the vent, sheet filter and filter cover as modified by the inventive concept, in an unassembled condition.
Figure 5:
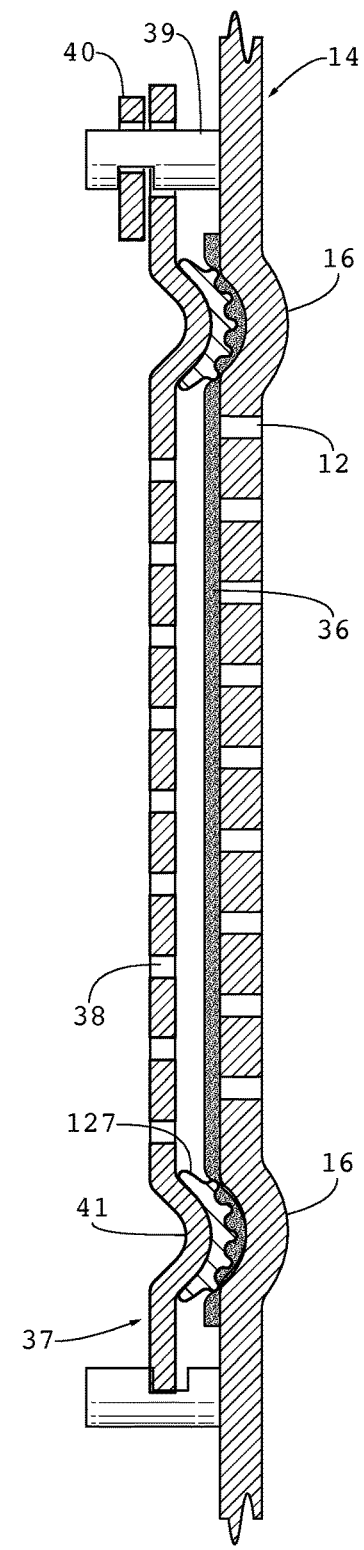
FIG. 5 is a side sectional view of FIG. 3; as seen along line 4-4 of FIG. 3 with the vent, sheet filter and filter cover as modified by the inventive concept in an assembled condition.

Attention is now directed to FIGS. 3 through 5, all of which are drawn from the teachings of the prior art Banks '032 patent, but which incorporate the teachings of the inventive concept. FIG. 3 is an exploded view that shows three distinct parts: the vent 23 and its surroundings on the sterilization container, a filter 36 and a filter cover 37, which holds the filter in registration on the vent. FIG. 4 is a side section view, taken along line 4-4 in FIG. 2, of the same three distinct parts, in an unassembled condition. FIG. 5 shows the same view as FIG. 4, but in an assembled condition. Be mindful that FIGS. 3 to 5 demonstrate the inventive concept and not the prior art.

Working from the bottom up in FIG. 3, the vent 23 with holes 12 and the posts 39 will be immediately recognized. However, where the Banks '032 patent would show the vent 23 surrounded by a concave surface (reference number 26 from FIG. 2) filled with a gasket, formed of a material having a soft DUROMETER rating, that is bonded into the concave surface, the gasket is not visible in FIG. 3, but it will be seen in an modified form as gasket 27 in FIGS. 4 and 5. This gasket 27 is preferably constructed of a temperature-tolerant material, such as silicone. The Banks '032 patent specifically teaches that, regardless of the geometry, the gasket 27 is in contact with substantially all of the surface of concave surface 26 and is wholly within the recess 26 so as not to extend above the planar surface 21 of lid 14, as is clearly seen in FIG. 5 (of both this application and Banks '032).

The second part shown in FIG. 3 is the sheet filter 36, which overlays the vent 23 at the interior surface 21. The sheet filter 36 is of sufficient width and length dimensions to lie upon not only the vent 23, but also the concave surface 26, preferably extending beyond the concave surface, thereby providing a good seal. To assist this, it would be known in this art to locate the posts 39 back from the concave surface 26.

The third part depicted in FIG. 3 is the generally planar filter cover 37 which has a pattern of cover holes 38. As is further seen in FIGS. 4 and 5, these cover holes 38 are typically offset from vent holes 12 when filter cover 37 is mounted and locked in position by posts 39 and a locking mechanism 40 (seen only in FIGS. 4 and 5). Mechanisms 40 for locking a filter cover 37 to a vent 23 using slots or aligning posts such as posts 39 and establishing positive pressure on the cover against the vent are well known in the art and therefore require no further description, although Banks '032 provides sufficient teaching.

In addition to the vent holes 38, FIG. 3 shows that filter cover 37 has a concave or recessed surface 41 on the surface 42 of the filter cover that faces into the interior of the sterilization container, that is, the upper surface of FIG. 3.

Keeping in mind that FIGS. 4 and 5 still reflect the inventive concept and not the prior art of the Banks '032 patent, it is noted that the vent ridge 16 extends above (the lid 14 is illustrated upside-down) the plane of the exterior surface 13 of lid 14 and surrounds the vent 23. In the preferred embodiment, the vent ridge 16 is the other side of the vent recess 26, although they could be separately formed. In either case, the recess and ridge co-act to protect the vent 23 from damage that could cause a breach of the seal.

In addition to the concave or recess surface 41 that surrounds cover holes 38 on side 42 of the filter cover 37, FIGS. 4 and 5 show that there is a cover ridge 43 on opposite side 44, the cover ridge surrounding the cover holes. The cover recess 41 and the cover ridge 43 can be formed as opposite sides of each other or separately.

As best seen in FIG. 5, when the vent cover 37 is locked in position over the vent 23 by a filter cover mounting and locking mechanism 39 and 40 with a sheet filter 36 therebetween (the sheet filter being sized to extend over and cover the vent recess), the cover ridge 43, as assisted by gasket 127 is forced against vent recess 26 with a positive pressure, causing filter 36 and gasket 127 to be compressed together between lid 14 and cover 37, establishing a fluid-tight seal surrounding the vent 23 and cover holes 38.

As seen in FIG. 5, and even though the recess 26 and ridge 43 may be approximately equal in size, the filter 36 and the gasket 127 cause a space 46 to be established therebetween when the cover 37 is fully engaged. This space, which is greater than the thickness of filter 36, plays an essential role in the movement of sterilization media through the vent 23.

Typically, during a sterilization cycle, sterilizing media enters the interior of the container 10 via the vent 23, through the sheet filter 36 which is disposed between the lid 14 and filter cover 37, while displaced atmosphere exits the same or another filtered vent. Any moisture formed in the sterilization container (not shown) is prevented from escaping the seal surrounding the vent and cover holes 38. Equally important, any fluid on the outside of the container near a vent is prevented from entering the container.

In the prior art, Banks '032 teaches that it is important, as seen in FIGS. 4 and 5, the provide a protected location, such as recess 26 for gasket 27. While this reduces the possibility of damage to the gasket, it also has the effect of reducing the surface area available for providing the sealing contact between the gasket 27 and the sheet filter 36. It also places the gasket 27 on either the lid 14 or on a surface of the container body 18. Either of these pieces will be at least as costly to replace as the vent cover 37.

It is useful at this point to discuss gasket 127 of the inventive concept. This A gasket 127 is at least placed atop ridge 43. and, in many embodiments, it can extend out onto This gasket 127 differs significantly from the gasket 27 of the Banks '032 prior art patent. First, it is placed atop ridge 43 and is not in any was associated with the recess 26 in lid 14. Second, and because it is atop the ridge 43, the outwardly facing surface 128 of the gasket 127 is convex and not concave. Third, and while Banks '032 contains no express teachings about the surface of gasket 27 that would be in contact with sheet filter 36, the outwardly facing surface 128 of gasket 127 preferably has one or more ridges 129 that extend outwardly, in a generally radial direction relative to the convex curvature if the surface 128. These ridges 129 are best viewed in FIG. 4. These ridges 129 allow for greater purchase of the sheet filter 36 when the filter cover is fixed to the lid or container body at a vent 23 using fixing means already described. Particularly, the ridges 129 can deform and a pair of the ridges can capture a portion of the filter between them. A fourth difference is that the gasket 127 may be provided with an inner and an outer lip that can extend onto surface 44 as the gasket is positioned on ridge 43. And, of course, gasket 127 can be bonded into place on ridge 43, in which case the respective lips provide an additional amount of surface area for the bonding.

These differences, when viewed as a whole, will be seen to provide the gasket 127 and the filter cover 37 with a significantly different and unexpectedly better operation.

Of course, various changes, modifications and alterations in the teachings of the present invention may be contemplated by those skilled in the art without departing from the intended spirit and scope thereof.

As such, it is intended that the present invention only be limited by the terms of the appended claims.

What is claimed is:

1. An arrangement for providing a sealed filtered vent for a sterilization container having a vent area formed by a plurality of holes passing through at least one of: a wall or a lid of the sterilization container, the vent area surrounded by a convex ridge on an outside surface of the wall or lid and a concave recess on an opposing inside surface, the arrangement comprising:
   a filter, sized and adapted to cover the vent area and overlie the concave recess;
   a filter cover plate, being of a generally planar nature with a vent area formed by a plurality of holes passing through the filter cover plate the vent area surrounded by a convex ridge, the convex ridge sized and adapted to correspond to the concave recess of the sterilization container;
   a gasket, secured to the filter cover plate along at least the convex ridge, the gasket having an outwardly-facing surface with at least two ridges that extend radially outwardly therefrom; and
   a means for mounting and securing the filter cover plate over the vent area on the wall or lid of the sterilization container, with the filter interposed and secured between the filter cover plate and the vent area on the inside surface of the wall or lid.

2. The arrangement of claim 1 wherein:
the means for mounting and securing effects a seal between the filter cover plate and the vent area on the inside surface of the wall or lid, by compressing the gasket into the filter.

3. The arrangement of claim 2, wherein:
the gasket comprises an elastomeric material.

4. The arrangement of claim 3, wherein:
the gasket comprises silicone.

5. The arrangement of claim 2, wherein:
the holes in the filter cover plate are offset from the holes in the vent area on the inside surface of the wall or lid, when the filter cover plate is mounted and secured by the mounting and securing means.

6. The arrangement of claim 1, wherein:
the mounting and securing means comprises a plurality of posts, arranged around a periphery of the vent area on the inside surface and a corresponding number of locking members that engage the filter cover plate.

7. The arrangement of claim 1, wherein:
the gasket has an outwardly-facing surface with at least two ridges that extend outwardly from the outwardly-facing surface.

8. The arrangement of claim 7, wherein:
the at least two ridges each extends radially outwardly from the outwardly-facing surface.

9. The arrangement of claim 1, wherein:
the gasket comprises an elastomeric material.

10. The arrangement of claim 9, wherein:
the gasket comprises silicone.

11. The arrangement of claim 1, wherein:
the holes in the filter cover plate are offset from the holes in the vent area on the inside surface of the wall or lid, when the filter cover plate is mounted and secured by the mounting and securing means.

12. A device for sealing a filter to a vent area of a sterilization container, the vent area formed by a plurality of holes passing through at least one of: a wall or a lid of the sterilization container, the vent area surrounded by a convex ridge on an outside surface of the wall or lid and a concave recess on an opposing inside surface, comprising the arrangement comprising:
   a filter cover plate, being of a generally planar nature with a vent area formed by a plurality of holes passing through the filter cover plate, the vent area surrounded by a convex ridge, the convex ridge sized and adapted to correspond to the concave recess of the sterilization container, and a gasket, secured to at least the convex ridge of the filter cover plate, the gasket formed from an elastomeric material and having an outwardly-facing surface with at least two ridges that extend radially outwardly from the outwardly-facing surface.

13. A sterilization container having a sealed filtered vent, comprising:

a vent area formed by a plurality of holes passing through at least one of: a wall or a lid of the sterilization container, the vent area surrounded by a convex ridge on an outside surface of the wall or lid and a concave recess on an opposing inside surface;

a filter, sized and adapted to cover the vent area and overlie the concave recess;

a filter cover plate, being of a generally planar nature with a vent area formed by a plurality of holes passing through the filter cover plate, the vent area surrounded by a convex ridge, the convex ridge sized and adapted to correspond to the concave recess of the sterilization container, and a gasket, secured to at least the convex ridge of the filter cover plate; and a means for mounting the filter cover plate over the vent area on the wall or lid of the sterilization container, with the filter interposed and secured between the filter cover plate and the vent area on the inside surface of the wall or lid.

* * * * *